United States Patent
Mollov et al.

(10) Patent No.: US 7,688,947 B2
(45) Date of Patent: Mar. 30, 2010

(54) METHOD FOR REDUCING SENSITIVITY MODULATION AND LAG IN ELECTRONIC IMAGERS

(75) Inventors: Ivan Petrov Mollov, Cupertino, CA (US); Carlo Alberto Tognina, Palo Alto, CA (US); Roberto Totaro, Zurich (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 281 days.

(21) Appl. No.: 11/582,637

(22) Filed: Oct. 17, 2006

(65) Prior Publication Data

US 2008/0094378 A1  Apr. 24, 2008

(51) Int. Cl.
*H05G 1/64* (2006.01)
*G01T 1/24* (2006.01)

(52) U.S. Cl. ............. 378/98.8; 250/370.08; 250/370.09
(58) Field of Classification Search .................. 378/19, 378/91, 96, 98.8, 98.9, 210; 250/370.01, 250/370.08, 370.09, 370.14
See application file for complete search history.

(56) References Cited

U.S. PATENT DOCUMENTS

| | | | |
|---|---|---|---|
| 4,697,280 A * | 9/1987 | Zarnstorff et al. ........... 378/207 |
| 4,823,178 A | 4/1989 | Suda | |
| 4,825,292 A * | 4/1989 | Knibbe ........................ 348/250 |
| 5,249,123 A | 9/1993 | Hsieh | |
| 5,319,206 A * | 6/1994 | Lee et al. ............... 250/370.09 |
| 5,331,145 A | 7/1994 | Weckler et al. | |
| 5,864,127 A | 1/1999 | Jackson | |
| 6,701,000 B1 | 3/2004 | Hsieh | |
| 6,718,010 B2 * | 4/2004 | Petrick et al. .............. 378/98.8 |
| 6,980,246 B1 * | 12/2005 | Ducourant et al. .......... 348/328 |
| 2002/0085108 A1 | 7/2002 | Hoffman | |

OTHER PUBLICATIONS

Varian, *International Preliminary Report on Patentability*, mailed Apr. 30, 2009; PCT Application No. PCT/US2007/021313.
Varian, *International Search Report and Written Opinion*, mailed Apr. 2, 2008; PCT Application No. PCT/US2007/021313.

* cited by examiner

*Primary Examiner*—Edward J Glick
*Assistant Examiner*—Anastasia Midkiff
(74) *Attorney, Agent, or Firm*—Blakely, Sokoloff, Taylor & Zafman LLP

(57) ABSTRACT

A method for reducing gain and lag signals associated with trapped charges is described. Data is collected from a detector. A forward bias voltage is temporarily applied to the detector between collecting the data.

35 Claims, 13 Drawing Sheets

METHOD FOR REDUCING SENSITIVITY MODULATION AND LAG IN ELECTRONIC IMAGERS

TECHNICAL FIELD

This invention relates to the field of an imaging system and, in particular, to solid state detectors.

BACKGROUND

A Computed Tomography system may collect data by using a large flat panel digital x-ray device, imager, or detector, having a plurality of pixels arranged in rows and columns. Large flat panel imagers function by accumulating charge on capacitors generated by the pixels of photodiodes (amorphous silicon or organic semiconductor) with scintillators or by pixels of photoconductors. Typically, many pixels are arranged over a surface of the imager where TFTs (or single and/or double diodes) at each pixel connect the charged capacitor to a read-out amplifier at the appropriate time. A pixel is composed of the scintillator/photodiode/capacitor/TFT or switching-diode combination or by the photoconductor/capacitor/TFT or switching-diode combination. Often the photodiode intrinsically has enough capacitance that no separate charge storage capacitor is required. Radiation (e.g., alpha, beta, gamma, X-ray, neutrons, protons, heavy ions, etc.) strikes the scintillator and causes the scintillator to generate visible light. The visible light strikes a phoiodiode and generates an electric current. Alternatively, an imager may be configured such that the radiation strikes a biased photoconductor to generate the electric current. The current charges a capacitor and leaves a charge on the capacitor. The integrated charge on the capacitor is proportional to the integrated light intensity striking the respective photoconductor for a given integration time. At an appropriate time, a switch (e.g., a TFT or switching diode(s)) activates and reads out the charge from the capacitor.

However, such flat panel imagers suffer from detector lag. The detector lag causes a significant portion of the signals from previous samples to incorrectly bias subsequent samples. A significant cause of the lag is related to the electron de-trapping resulting from the high density electronic defects in the energy band gap. De-trapping times range from a few milliseconds to as long as 100 seconds, days, weeks, or even months. As a result of the non-uniformity of the lag, artifacts, such as rings and bands, occur in the reconstructed images.

Prior correction methods have been implemented to estimate offset correction. One prior background correction method discussed in U.S. Pat. No. 5,249,123 applies a filter function to the output signal. Another prior background correct method discussed in U.S. Pat. No. 6,701,000 energizes each detector pixel to reduce residual signal in-between data acquisitions when the x-ray emission is stopped. LEDs that are built into the panel saturate the traps in the detector, which minimize the temporal artifacts. However, exposing each detector pixel to an evenly distributed light complicates the mechanical construction of flat panel imagers and increases their manufacturing costs. Furthermore, the LEDs and the light distribution can interfere with x-ray beams that need to be imaged.

BRIEF DESCRIPTION OF THE DRAWINGS

The present invention is illustrated by way of example, and not by way of limitation, in the figures of the accompanying drawings.

DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of the present invention include various operations, which will be described below. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

Figure 1A:
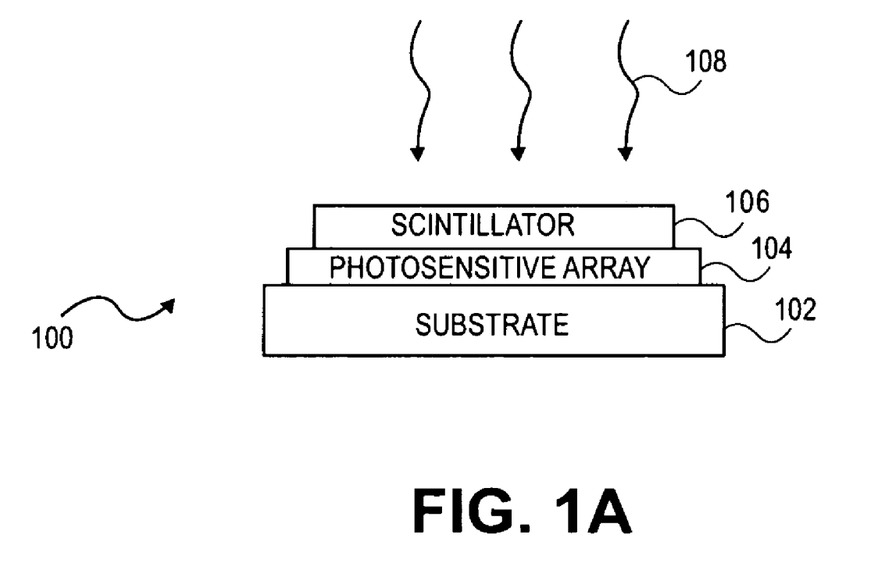
FIG. 1A is a schematic diagram illustrating one embodiment of a detector.

FIG. 1A is a schematic diagram illustrating one embodiment of a detector 100. The detector 100 may be a solid-state detector or radiation imager in a large flat panel configuration having a photosensor array 104 disposed on a substrate 102 and a scintillator 106 disposed on the photosensor array 104. Scintillator 106 is disposed so as to receive and absorb incident radiation, e.g., x-ray beam 108. Scintillator 106 is optically coupled to photosensor array 104 so that optical photons generated in scintillator 106 pass into photosensor array 104. Photosensor array 104 may include a plurality of photosensors (not shown), such as photodiodes, and an addressable thin film transistor (TFT) array (not shown) electrically coupled to each photosensor. In one embodiment, each photosensor includes an amorphous silicon (a-Si) photodiode (not shown).

Figure 1B:
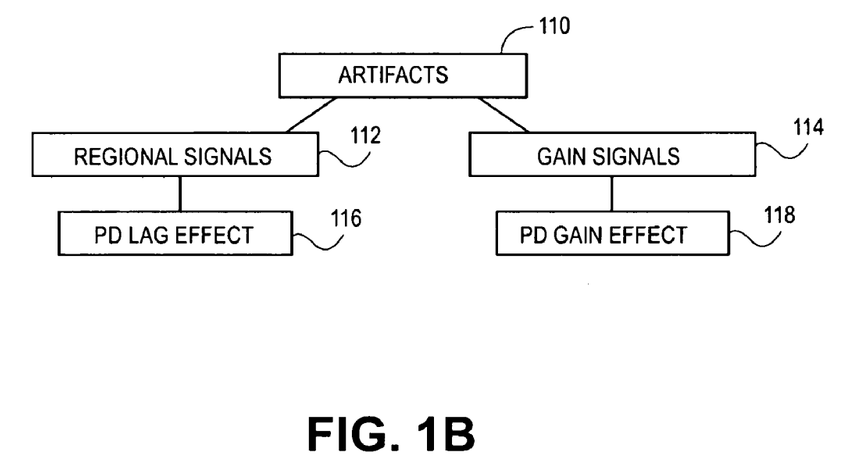
FIG. 1B is a schematic diagram of a classification of the artifacts and their sources.

FIG. 1B is a schematic diagram of a classification of the artifacts and their sources. Artifacts 110 may include residual signals 112 of a detector and gain effects 114 from the traps already filled in the detector. The residual signals 112 may be caused by the photodiode (PD) lag effect 116. The gain effects 114 may be caused by the PD gain effect 118.

Figure 2:
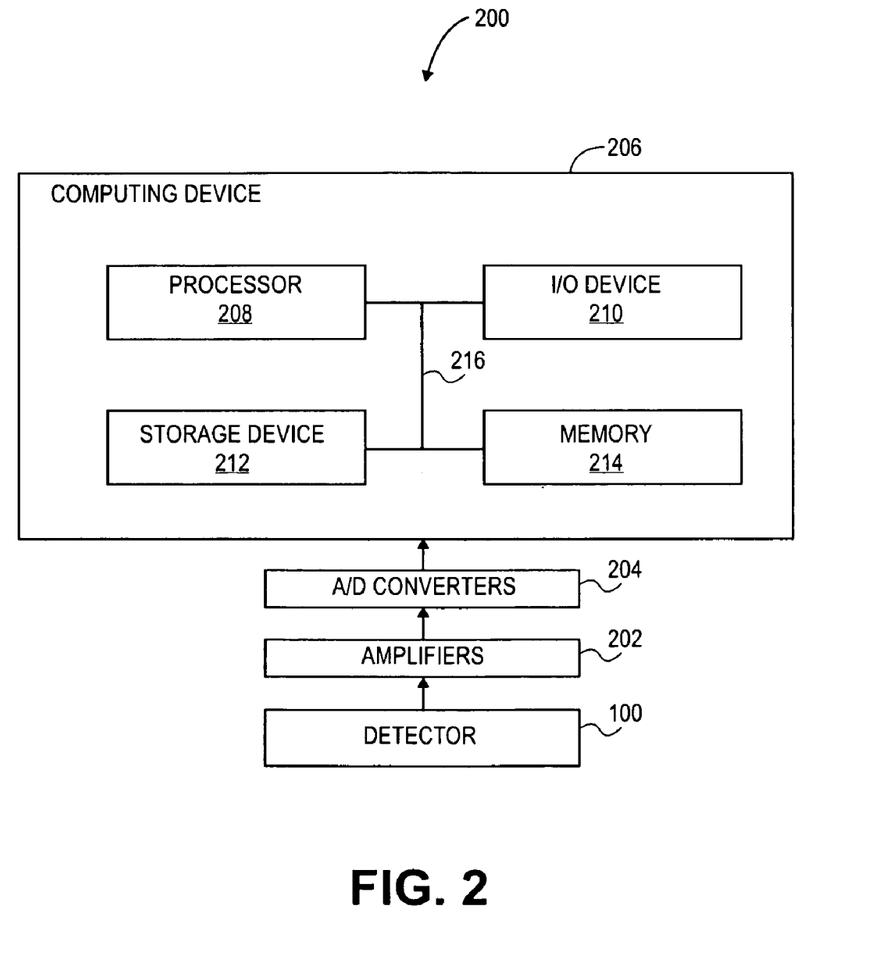
FIG. 2 is a schematic diagram illustrating one embodiment of an imaging system.

FIG. 2 is a schematic diagram illustrating one embodiment of an imaging system. Imaging system 200 includes a computing device 206 coupled to detector 100. The detector 100, may be also, for example, an amorphous silicon organic semiconductor TFT or diode-switched array imager. As previously discussed in FIG. 1, detector 100 functions by accumulating charge on capacitors generated by pixels of photodiodes (amorphous silicon or organic semiconductor) with scintillators or by pixels of biased photoconductors. Typically, many pixels are arranged over a surface of the detector 100 where, for example, TFTs (or single and/or double diodes) at each pixel connect a charged capacitor to charge sensitive amplifier 202 at the appropriate time. Charge sensitive amplifiers 202 drive analog to digital (A/D) converter 204 that, in turn, converts the analog signals received from amplifiers 202 into digital signals for processing by computing device 206. A/D converter 204 may be coupled to computing device 206 using, for example, I/O device 210 or interconnect 216. A/D converter 204 and charge sensitive amplifiers 202 may reside within computing device 206 or detector 100 or external to either device.

Computing device 206 implements the methods for correction of imaging sensors due to the traps from the detector 100. The methods that may be performed by computing device 206 constitute computer programs made up of computer-executable instructions illustrated as steps in the following examples of the methods illustrated in the following figures. In one embodiment, computing device 206 includes a processor 208, storage device 212, input/output (IO) device 210, and memory 214 that are all coupled together with interconnect 216, such as a bus or other data path. In another embodiment, the computing device may be implemented using Programmable Logic Devices (PLD) or Field Programmable Gate Arrays (FPGA), in which the mathematical operations are performed by physical devices like adders, multipliers, etc. In another embodiment, the computing device may be implemented using specialized integrated circuits for data processing like adders, multipliers, bus switches, registers, RAM, ROM logic gates, etc.

Processor 208 represents a central processing unit of any type of architecture (e.g., Intel architecture or Sun Microsystems architecture), or hybrid architecture. In addition, processor 208 could be implemented in one or more semiconductor chips. In an alternative embodiment, for example, the processor 208 may be a network processor having multiple processors including a core unit and multiple microengines. Additionally, processor 208 may include any combination of general-purpose processing device(s) and special-purpose processing device(s).

Storage device 212 represents one or more mechanisms for storing data and/or instructions such as the method steps of the invention. Storage device 212 represents read-only memory (ROM), random access memory (RAM), magnetic disk storage media, optical storage media, flash memory devices, and/or other machine-readable media. Interconnect 216 represents one or more buses (e.g., accelerated graphics port bus, peripheral component interconnect bus, industry standard architecture bus, X-Bus, video electronics standards association related buses, etc.) and bridges (also termed bus controllers). I/O device 216 represents any of a set of conventional computer input and/or output devices including, for example, a keyboard, mouse, trackball or other pointing device, serial or parallel input device, display monitor, plasma screen, or similar conventional computer I/O devices.

Memory 214 represents a high-speed memory device for retaining data and processor instructions for processor 208 according to the method steps of the invention. Memory 214 can be implemented using any of the memory devices described above for storage device 212. In addition, memory 214 can be used as a data cache for processor 208. While this embodiment is described in relation to a single processor computer system, in another embodiment, the invention may be implemented in a multi-processor computer system.

To keep the amorphous Silicon traps in the detector in a steady state, a forward bias current is periodically applied to the diodes, or photodiodes. This forward bias current provides the free carries necessary to keep a majority of the trap states occupied. The time interval between applying the forward bias current can be selected depending on the application.

In accordance with one embodiment, a forward bias current pulse is applied for each frame. As such, photodiode gain and lag effects are reduced significantly and uniformly for all exposures.

In accordance with another embodiment, a forward bias current cycle may be used to fill the amorphous Silicon trap states before the start of an image acquisition sequence. This effectively "erases" the exposure history of the detector by filling all traps uniformly, effectively setting the imaging system into a known state.

In accordance with other embodiments, if pixels with open TFT's can be assumed "floating", one could switch all pixels from a negative to a positive bias voltage without changing the voltage across these diodes but by just shifting their potential in reference to the ground. Pixels with open TFTs would therefore still integrate charge generated by light photons and only pixels with closed TFTs would see a forward bias current. This embodiment allows an implementation of the forward bias current method which is compatible with continuous x-ray exposure.

Figure 3A:
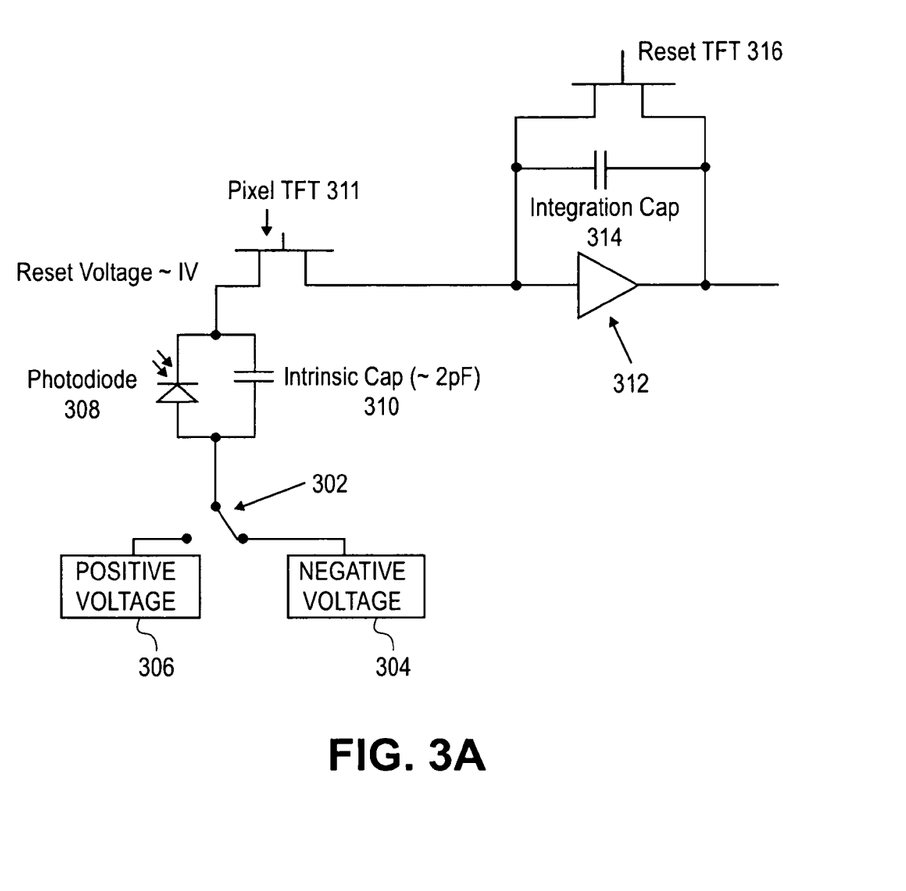
FIG. 3A is a schematic circuit diagram illustrating one embodiment of a detector.
Figure 3B:
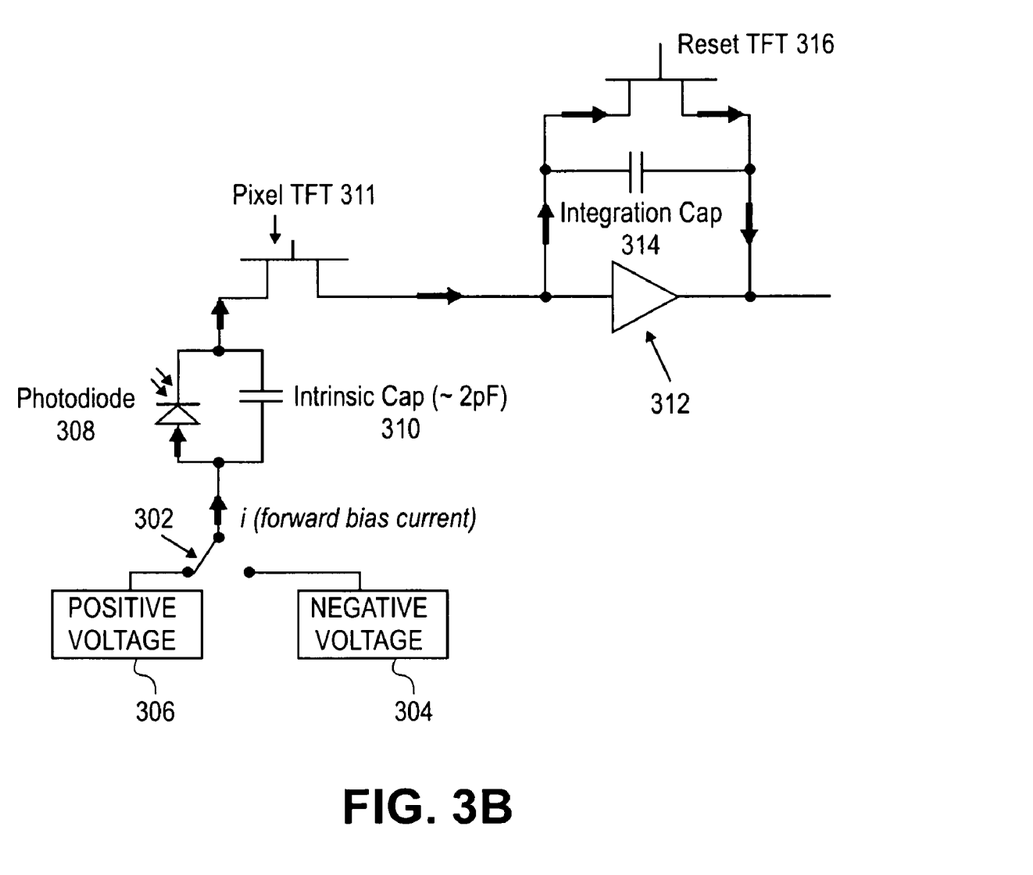
FIG. 3B is a schematic circuit diagram illustrating one embodiment of a detector.

FIGS. 3A and 3B are schematic circuit diagrams illustrating one embodiment of a detector. A switch 302 switches a connection between a negative bias voltage source 304, as illustrated in FIG. 3A, and a positive bias voltage 306, as illustrated in FIG. 3B. A photodiode 308 is connected in parallel with a capacitor 310. The capacitor may be, for example, an intrinsic capacitor of about 2 pF. However, other types of capacitors of different capacitances may also be used.

Both the capacitor 310 and the cathode end of the photodiode 308 are connected to a switch, such as a pixel Thin Film Transistor (TFT) 311. Other types of switches may also be used. An amplifier, such as a Charge Integration Amplifier 312, may be connected to an end of the pixel TFT 311. The amplifier may also include an integration capacitor 314 and another switch, such as a reset TFT 316.

FIG. 3A illustrates a photodiode and its associated TFT and charge integration amplifier configured for a normal reversed bias photodiode operation. The negative voltage source may generate a negative voltage of, for example, about −4.5V. The anode end of the photodiode 308 is connected to the switch 302. As such, the anode potential of the photodiode 308 can be switched from the normal negative bias voltage from the negative voltage source 304 to a positive voltage from the positive voltage source 306. The control of the switch 302 may be implemented into the software or hardware of the imaging system 200.

The forward bias cycle is initialized by applying a positive voltage to the photodiode anode, e.g. switching the switch to connect to the positive voltage source 306. Then, both the pixel TFT 311 and the reset TFT 316 of the charge integration amplifier 312 are closed to allow the current to flow. A forward current (indicated by the arrows in FIG. 3B) flows through the photodiode 308, providing free carriers to fill available amorphous Silicon traps. The forward bias cycle is terminated by opening the two TFT's 311, 316 and then reapplying a negative bias voltage to the anode of the photodiode 308 such that the photodiode 308 is reversed bias.

In accordance with one embodiment, prior to an x-ray exposure, the photodiodes may be reset to their reversed bias state. This is accomplished by closing both TFT 311, 316 for an appropriate duration. Optionally, this reset cycle may be repeated a second time after several milliseconds to ensure that potential disturbances created by the forward bias cycle would not affect the reset state of the photodiode 308. Once reset, the system is ready for the next x-ray exposure and signal readout after which the next forward bias cycle is started.

FIG. 3B illustrates how the current forward bias flows through the circuit when switch 302 is connected to the positive voltage source. Both TFT 311, and 316 are shown closed allowing the current to freely flow through. When the forward bias current flows through photodiode 308, a majority of the trap states in the photodiode 308 is occupied.

Figure 4:
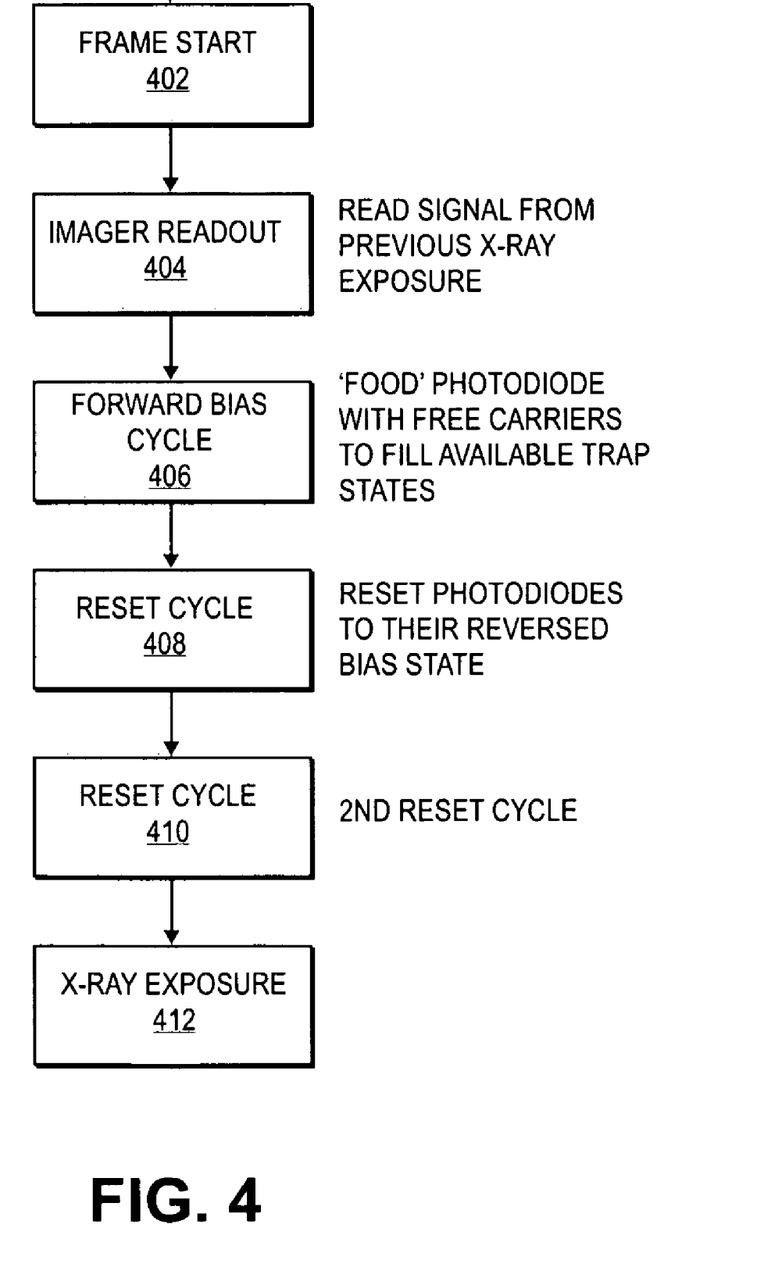
FIG. 4 is a flow diagram illustrating one embodiment of a method for operating the detector of FIG. 3.

FIG. 4 is a flow diagram of a frame-by-frame forward bias method. At 402, an x-ray beam is projected onto a detector of an imaging system as previously described in FIG. 2 to start a frame. At 404, the detector read signal from the previous x-ray exposure in 402. At 406, a forward bias cycle is applied to the detector to "flood" the photodiodes with free carriers to fill the available trap states. At 408, the photodiodes are reset back to their reversed bias state. At 410, a second reset cycle may be optionally applied. The imaging system is now ready for the next x-ray exposure at 412.

Figure 5:
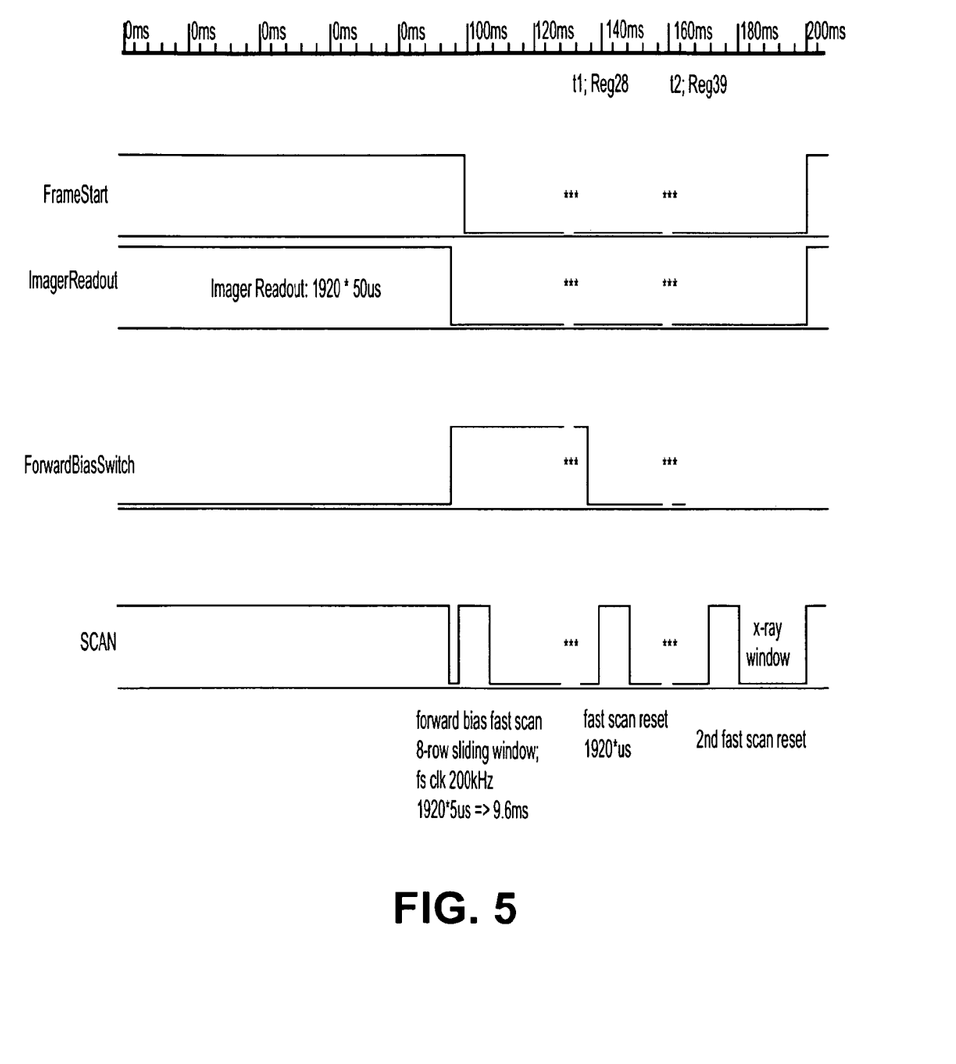
FIG. 5 is a schematic timing diagram illustrating one embodiment of readout of the detector of FIG. 3.

FIG. 5 is a schematic timing diagram of the method of FIG. 4. The frame start line 502 illustrates a period of time when the detector is exposed with x-ray. The imager readout line 504 illustrates a period of time when the detector detects the x-ray from the x-ray beams. The forward bias switch line 506 illustrates a period of time when the switch 302 is connected to the positive voltage source 306. The scan line 508 illustrates a period of time when resets are being applied to the detector. The forward bias switch is enabled as illustrated in 506 upon the detector finishing with the readout as illustrated in 504.

Figure 6:
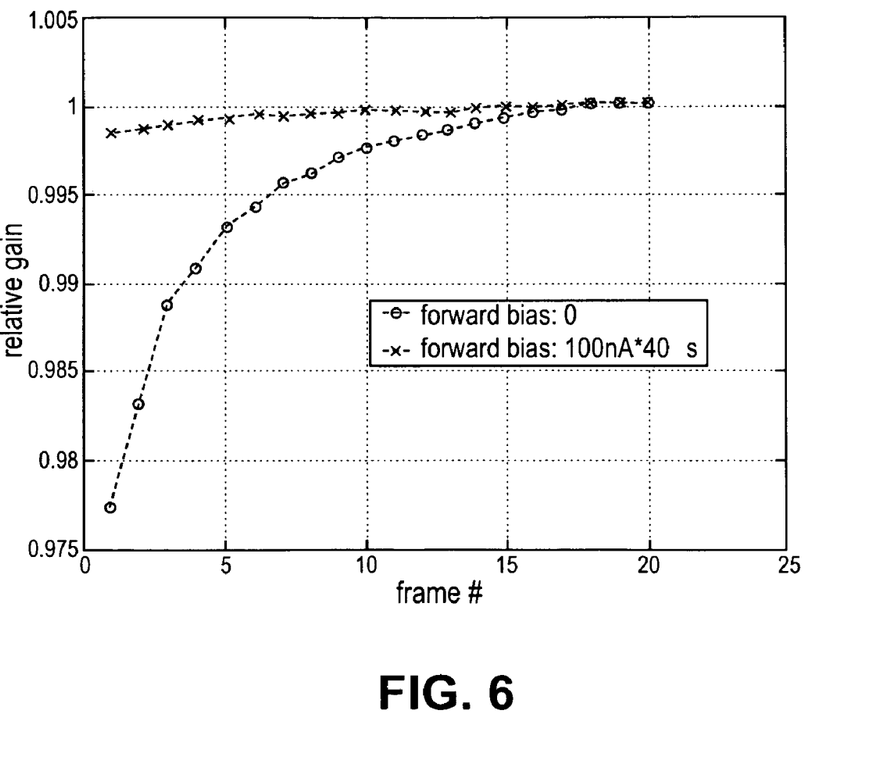
FIG. 6 is a graph diagram illustrating a relative gain as a function of frame number.

FIG. 6 is a graph diagram illustrating a relative gain as a function of frame number. The gain effects with forward bias current and without forward bias current are shown. Without forward bias, there is approximately a 2.3% gain change from frame 1 to frame 20. With a forward bias cycle of 100 nA*40 us per diode, this gain change is reduced to approximately 0.2%.

Figure 7:
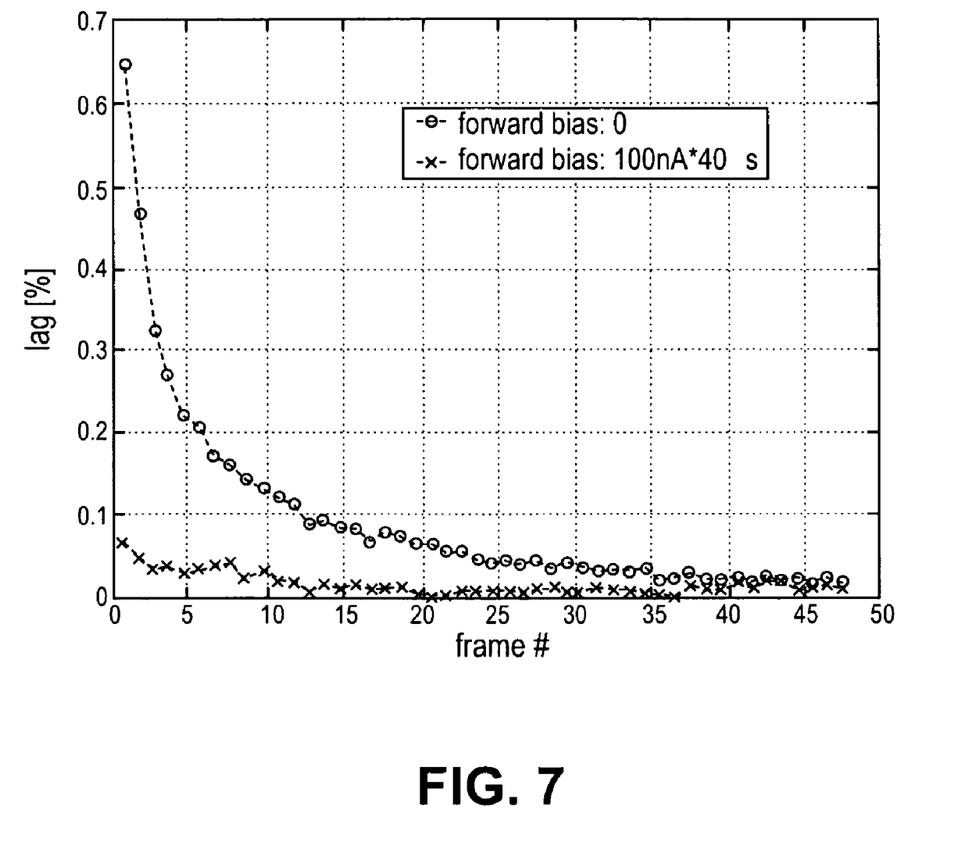
FIG. 7 is a graph diagram illustrating a relative lag as a function of frame number.

FIG. 7 is a graph diagram illustrating a relative lag as a function of frame number. The graph shows similar improvement between a relative lag without forward bias current and with forward bias current.

Figure 8:
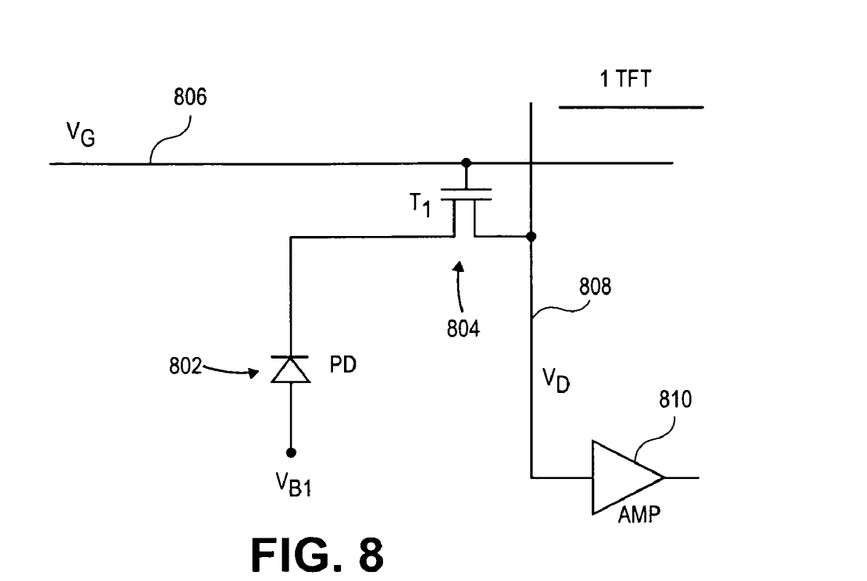
FIG. 8 is a schematic circuit diagram illustrating another embodiment of a detector.

FIG. 8 is a schematic circuit diagram illustrating another embodiment of a detector with one transistor. The anode end of a photodiode 802 is connected to a voltage source VB1. The cathode end of the photodiode 802 is connected to a transistor 804 (e.g. a TFT T1). The transistor 804 may be connected to a voltage line VG 806 and a voltage line VD 808 of an amplifier 810.

Figure 9:
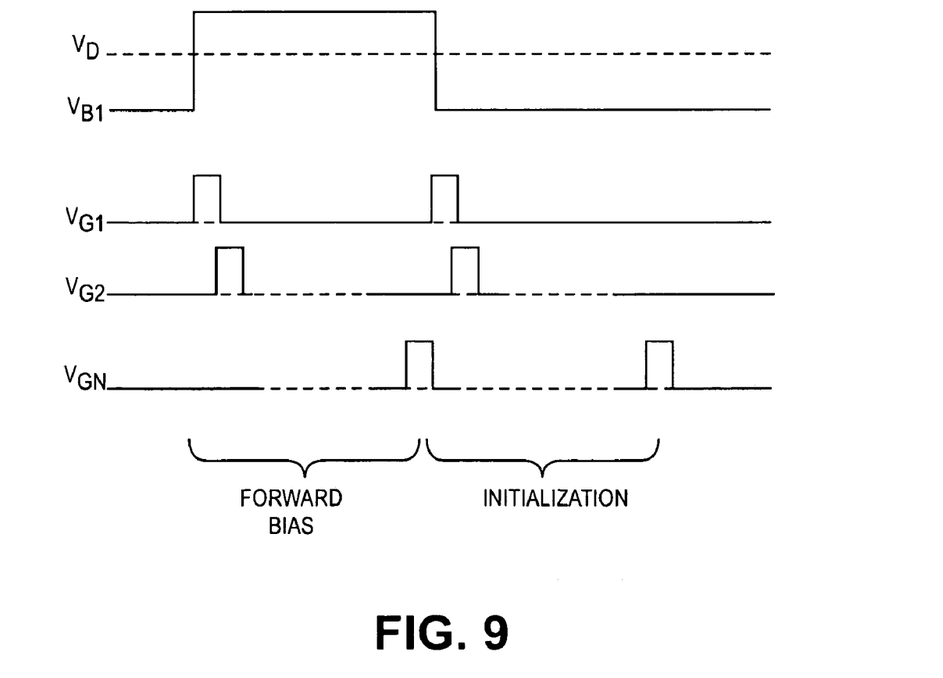
FIG. 9 is a schematic timing diagram illustrating one embodiment of readout of the detector of FIG. 8.

FIG. 9 is a schematic timing diagram illustrating one embodiment of readout of the detector of FIG. 8. A forward bias current can be applied across the photodiode 802 when voltage source VB1 is greater than voltage line VD.

Figure 10:
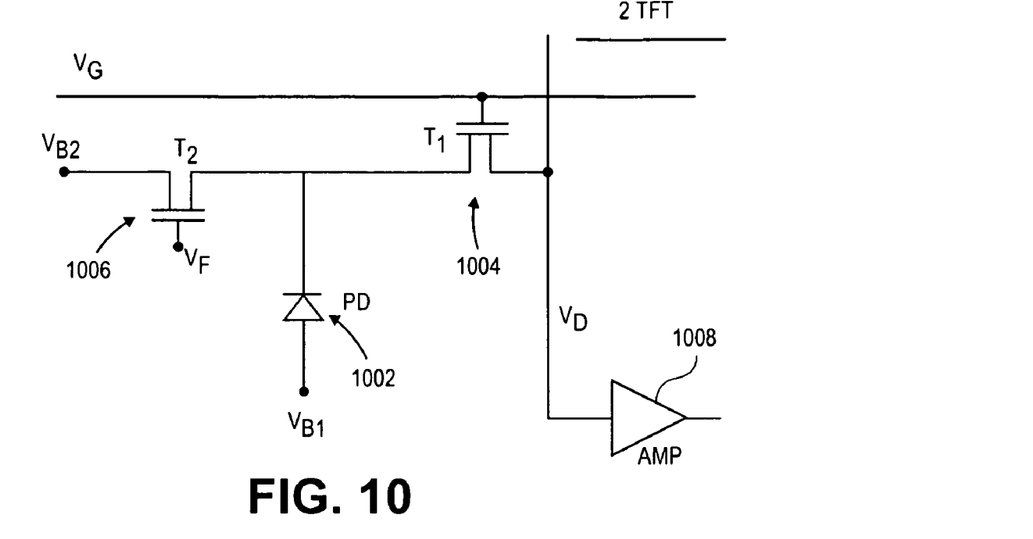
FIG. 10 is a schematic circuit diagram illustrating another embodiment of a detector.

FIG. 10 is a schematic circuit diagram illustrating another embodiment of a detector with two transistors. The anode end of a photodiode 1002 is connected to a voltage source VB1. The cathode end of the photodiode 1002 is connected to a first transistor T1 1004, and a second transistor T2 1006. Transistor T1 1004 is connected to a voltage line VD of an amplifier 1008 and a voltage line VG. Transistor T2 1006 is connected to a voltage line VB2 and a voltage line VF.

Figure 11:
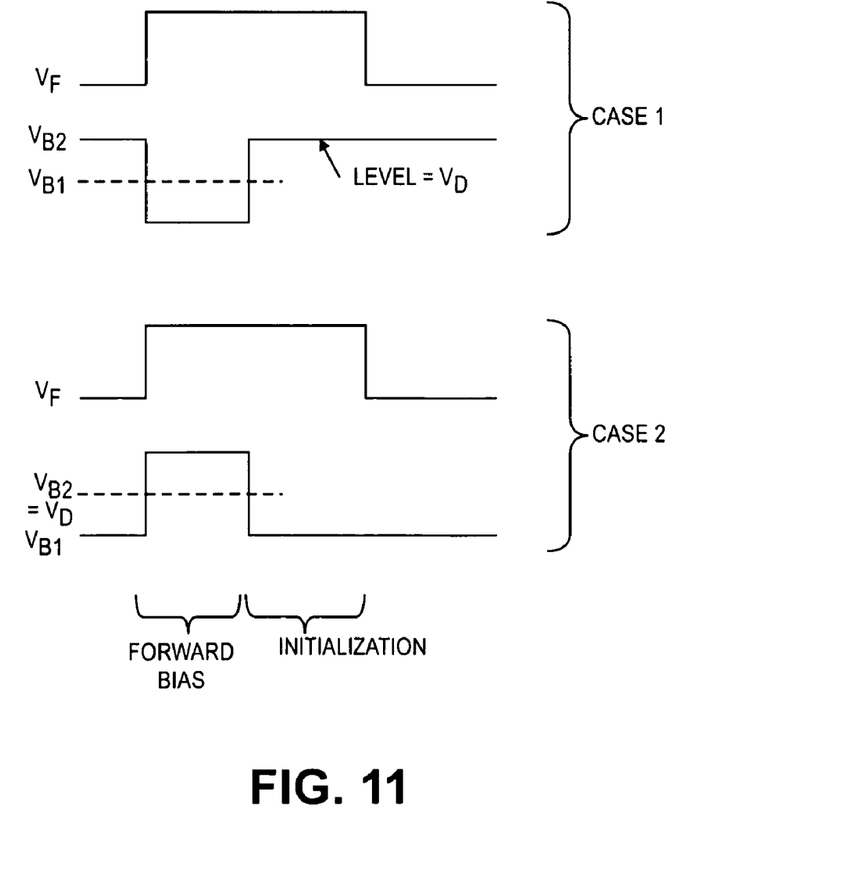
FIG. 11 is a schematic timing diagram illustrating one embodiment of readout of the detector of FIG. 10.

FIG. 11 is a schematic timing diagram illustrating one embodiment of readout of the detector of FIG. 10. In accordance with a first embodiment, a forward bias current can be applied to the photodiode 1002 when VB2 is less than VB1, and VB2 is substantially equal to VD. In accordance with a second embodiment, a forward bias current can be applied to the photodiode 1002 when VB2 is greater than VB1, and VB2 is substantially equal to VD.

Figure 12:
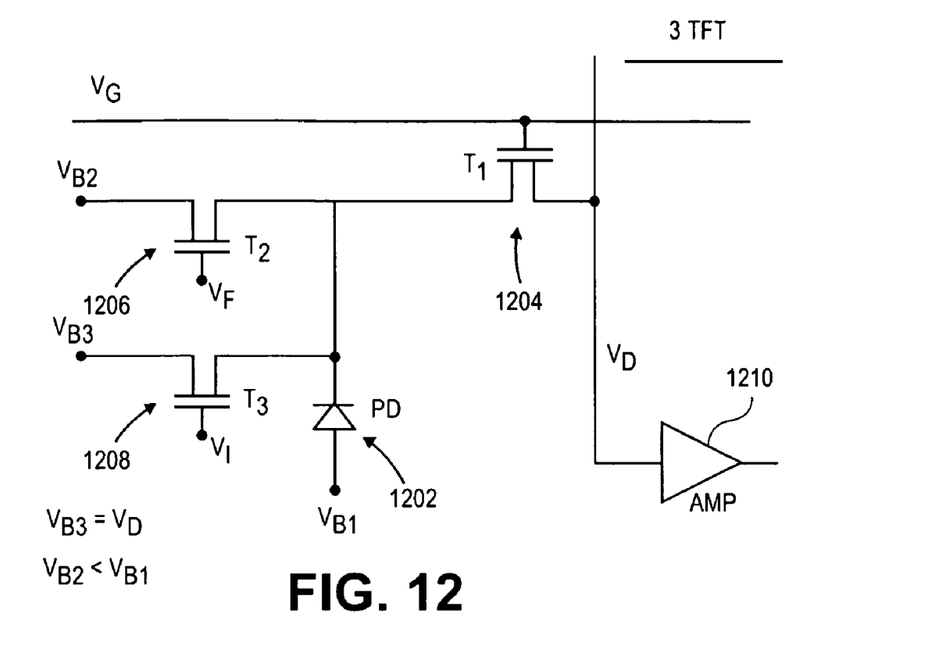
FIG. 12 is a schematic circuit diagram illustrating another embodiment of a detector.

FIG. 12 is a schematic circuit diagram illustrating another embodiment of a detector with three transistors. The anode end of a photodiode 1202 is connected to a voltage source VB1. The cathode end of the photodiode 1202 is connected to a first transistor T1 1204, a second transistor T2 1206, and a third transistor T3 1208. Transistor T1 1204 is connected to a voltage line VD of an amplifier 1210 and a voltage line VG. Transistor T2 1206 is connected to a voltage line VB2 and a voltage line VF. Transistor T3 1208 is connected to a voltage line VB3 and a voltage line VI.

The potential of voltage line VB3 is substantially equal to the potential of voltage line VD. The potential of voltage line VB2 is less than the potential of voltage line VB1.

Figure 13:
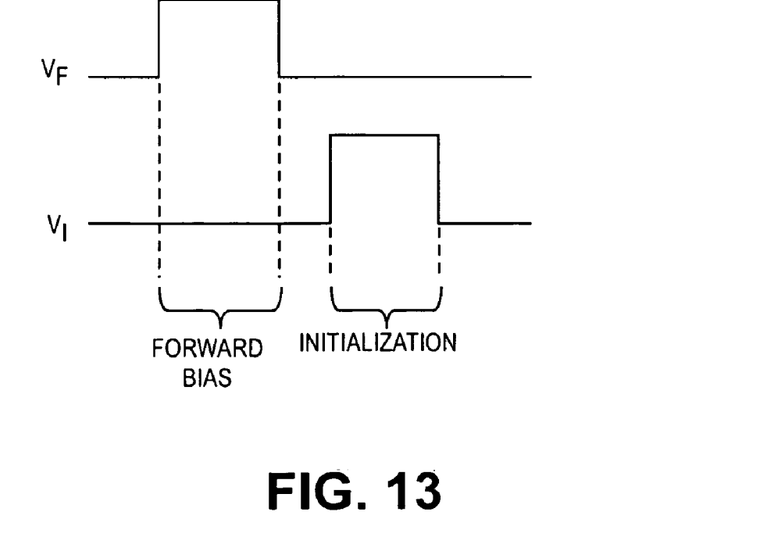
FIG. 13 is a schematic timing diagram illustrating one embodiment of readout of the detector of FIG. 12.

FIG. 13 is a schematic timing diagram illustrating one embodiment of readout of the detector of FIG. 12. A forward bias current can be applied across the photodiode 1202 when the potential voltage source VF is relatively increased.

Figure 14:
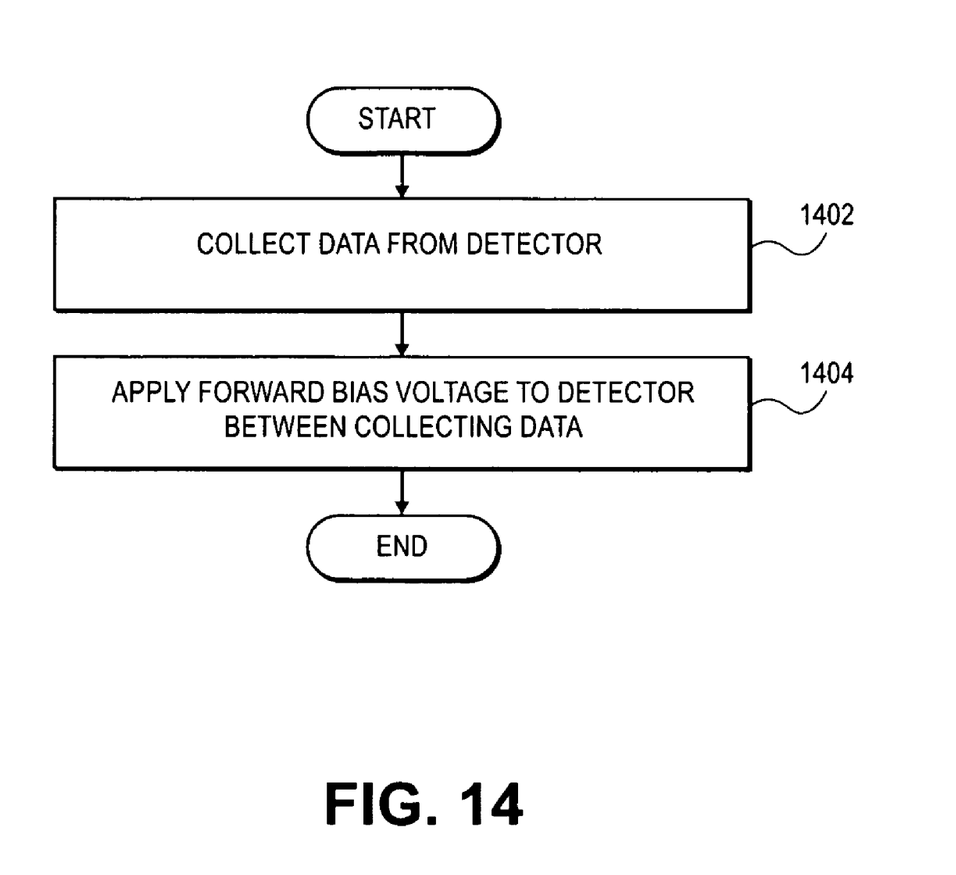
FIG. 14 is a flow diagram illustrating a method for correcting an output of a detector in accordance with one embodiment.

FIG. 14 is a flow diagram illustrating a method for correcting an output of a detector in accordance with one embodiment. At 1402, data is collected from the detector. At 1404, a forward bias current is temporarily applied to the detector between collecting data. Those of ordinary skills in the art will recognize that there exist many other ways of applying a forward bias current. Other embodiments of the present invention also include any means for applying enough voltage to pass a current to inject carriers into regions to fill the traps in the solid state detector. Some examples were previously described. The voltage lines may be switched so as to apply a forward bias current. The potential of one of the voltage line may be lowered so as to apply a forward bias current.

Those of ordinary skills in the art will recognize that there are other variations of the presently described embodiments to substantially filling traps in the detector based on the detector circuits illustrated in FIGS. 3A, 3B, 8, 10, 12. For example, all the "anode" and "cathode" along with the voltage polarity in all the illustrated circuits may be reversed to yield the same result.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
   collecting data from a detector, the detector connected to a pixel Thin Film Transistor (TFT) and a reset TFT in series;
   applying a forward bias voltage to the detector between collecting data while closing the pixel TFT and the reset TFT;
   opening the pixel TFT and the reset TFT and applying a reverse bias voltage to the detector; and
   resetting the detector by closing the pixel TFT and the reset TFT for a predetermined amount of time for one or more cycle while applying the reverse bias voltage to the detector.

2. The method of claim 1, wherein the detector further comprises a photosensor.

3. The method of claim 2, wherein the photosensor includes an amorphous silicon photodiode.

4. The method of claim 1, wherein the detector is to receive an x-ray beam from an x-ray source.

5. The method of claim 4, further comprising:
   disabling the x-ray source between collecting data.

6. The method of claim 1, wherein applying the forward bias voltage further comprises:
   switching to the forward bias voltage between collecting data; and
   switching to the reverse bias voltage while collecting data.

7. The method of claim 1, further comprising:
   applying a forward bias voltage to the detector in a cyclical period.

8. The method of claim 1, wherein applying the forward bias voltage further comprises:
   connecting a cathode end of the detector with a potential lower than that of an anode end of the detector.

9. A detector comprising:
   a photosensor circuit having a photodiode connected to a pixel TFT and a reset TFT in series; and
   a switch coupled to the photosensor circuit,
   wherein the switch is coupled to a first voltage source to forward bias the photodiode, and is coupled to a second voltage source to reverse bias the photodiode.

10. The detector of claim 9, wherein a potential of the first voltage source is higher than the potential of the second voltage source.

11. The detector of claim 10, wherein the first voltage source includes a positive voltage, and the second voltage source includes a negative voltage.

12. The detector of claim 9, wherein the switch couples the photosensor circuit to the first voltage source between collections of data from the detector.

13. The detector of claim 9, wherein the switch couples the photosensor circuit to the first voltage source after each frame detected by the detector.

14. The detector of claim 9, wherein the photosensor circuit further comprises:
   a photodiode coupled to a capacitor;
   the pixel TFT coupled to the photodiode and the capacitor; and
   an amplifier coupled to the pixel TFT.

15. The detector of claim 14, further comprising:
   the reset TFT coupled to the amplifier in parallel to reset a readout cycle of the detector.

16. The detector of claim 15, wherein the pixel TFT is coupled to a cathode end of the photodiode.

17. The detector of claim 16, wherein the switch is coupled to an anode end of the photodiode.

18. The detector of claim 9, wherein the photosensor is to detect an x-ray beam from an x-ray source.

19. An imaging system comprising:
   a source of radiation;
   a detector for sensing radiation from the source and generating data representative of the radiation, the detector comprising a photodiode coupled to a pixel TFT and a reset TFT in parallel; and
   a processor coupled to the detector and configured to switch a voltage applied to the detector between a first voltage source to forward bias the photodiode, and coupled to a second voltage source to reverse bias the photodiode, and to reset the detector by closing the pixel TFT and the reset TFT for a predetermined amount of time for one or more cycle while applying the second voltage source to the detector.

20. The imaging system of claim 19, wherein the source of radiation includes an x-ray source emitting an x-ray beam.

21. The imaging system of claim 19, wherein the detector further comprises at least one solid state x-ray detector.

22. The imaging system of claim 19, wherein the detector further comprises:
   a photosensor circuit; and
   a switch coupled to the photosensor circuit,
   wherein the switch is coupled to the first voltage source and the second voltage source.

23. The imaging system of claim 19, wherein a potential of the first voltage source is higher than the potential of the second voltage source.

24. The imaging system of claim 23, wherein the first voltage source includes a positive voltage, and the second voltage source includes a negative voltage.

25. The imaging system of claim 22, wherein the switch couples the photosensor circuit to the first voltage source between collections of data from the detector.

26. The imaging system of claim 25, wherein the switch couples the photosensor circuit to the first voltage source after each frame detected by the detector.

27. The imaging system of claim 22, wherein the photosensor circuit further comprises:
   a photodiode coupled to a capacitor;
   the pixel TFT coupled to the photodiode and the capacitor; and
   an amplifier coupled to the pixel TFT.

28. The imaging system of claim 27, further comprising:
   the reset TFT coupled to the amplifier to reset a readout cycle of the detector.

29. The imaging system of claim 28, wherein the first switch is coupled to a cathode end of the photodiode.

30. The imaging system of claim 29, wherein the switch is coupled to an anode end of the photodiode.

31. The imaging system of claim 19, wherein traps in the detector are substantially filled when the voltage is switched from the second voltage source to the first voltage source.

32. The method of claim 1, wherein collecting further comprises collecting data from a plurality of photodiodes of the detector, the detector including a plurality of pixel TFTs, and a plurality of reset TFTs, the photodiodes each connected to a pixel TFT and a reset TFT in series;
   wherein applying further comprises applying a forward bias voltage to the plurality of photodiodes between collecting data while closing the pixel TFTs and the reset TFTs;
   wherein opening further comprises opening the pixel TFTs and the reset TFTs and applying a reverse bias voltage to the plurality of photodiodes; and
   wherein resetting further comprises resetting the plurality of photodiodes by closing the pixel TFTs and the reset TFTs for a predetermined amount of time for one or more cycles while applying the reverse bias voltage to the plurality of photodiodes.

33. The method of claim 1, wherein applying further comprises switching a switch in series with an anode of a photodiode to a positive bias voltage to apply the forward bias voltage to the photodiode between collecting data while closing the pixel TFT and the reset TFT;
   wherein opening further comprises opening the pixel TFT and the reset TFT and switching the switch to a negative bias voltage to apply a reverse bias voltage to the photodiode.

34. The detector of claim 9, wherein the detector further comprises:
   a plurality of photosensor circuits having photodiodes each connected to a pixel TFT and a reset TFT in series to reset each photodiode by closing the pixel TFT and the reset TFT for a predetermined amount of time for one or more cycles while applying the reverse bias voltage to the photodiode.

35. The imaging system of claim 19, wherein the system further comprises at least one switch coupled in series with an anode of the photodiode to switch the voltage applied to the detector from the first voltage source to forward bias the photodiode.

* * * * *